United States Patent [19]

Boschelli et al.

[11] Patent Number: 5,489,586
[45] Date of Patent: Feb. 6, 1996

[54] METHOD FOR TREATING INFLAMMATORY DISEASE IN HUMANS

[75] Inventors: Diane H. Boschelli, Plymouth; David T. Connor, Ann Arbor, both of Mich.; James B. Kramer, Sylvania, Ohio; Paul C. Unangst, Ann Arbor, Mich.

[73] Assignee: Warner-Lambert Company, Morris Plains, N.J.

[21] Appl. No.: 351,611

[22] Filed: Dec. 12, 1994

Related U.S. Application Data

[63] Continuation-in-part of Ser. No. 207,330, Mar. 7, 1994, abandoned.

[51] Int. Cl.[6] .................. A61K 31/55; C07D 513/04
[52] U.S. Cl. .................. 514/211; 514/220; 540/495
[58] Field of Search .................. 514/211, 220

[56] References Cited

U.S. PATENT DOCUMENTS 4,013,641  3/1977  Brown .................. 260/239

FOREIGN PATENT DOCUMENTS

94/17075  4/1994  WIPO .................. 540/495

OTHER PUBLICATIONS

PCT Search Report, PCT/US 95/01275.
*Chemical Abstracts*, vol. 105, No. 25, 1986, abstract No. 226266q, Nagarajan et al.
*Chemical Abstracts*, vol. 115, No. 21, 1991, abstract No. 232194n, Hiremath et al.
*Chemical Abstracts*, vol. 89, No. 5, 1978, abstract No. 43178u, Glushkov et al.

*Primary Examiner*—Robert T. Bond
*Attorney, Agent, or Firm*—Charles W. Ashbrook

[57] ABSTRACT

Benzothiophene, benzofuran and indole-thiazepinones, oxazepinones and diazepinones as well as methods of preparation thereof are described as agents which inhibit leukocyte adherence to vascular endothelium and, as such, are effective therapeutic agents for treating inflammatory diseases.

4 Claims, No Drawings

METHOD FOR TREATING INFLAMMATORY DISEASE IN HUMANS

CROSS REFERENCE TO RELATED APPLICATIONS

This is a continuation-in-part of U.S. Ser. No. 08/207,330 filed Mar. 7, 1994, now abandoned.

BACKGROUND OF THE INVENTION

The present invention is for novel benzothiophene, benzofuran and indole thiazepinones, oxazepinones and diazepinones and pharmaceutically acceptable salts thereof, used to prevent the adhesion of leukocytes to endothelial cells. Leukocyte adherence to vascular endothelium is integral to the pathogenesis of inflammation. The adhesion process precedes transendothelial migration of leukocytes into surrounding tissue and ensuing tissue damage. Compounds that can block this initial adhesive interaction are expected to have efficacy in the treatment of inflammatory diseases such as rheumatoid arthritis, osteoarthritis, asthma, and psoriasis. Other indications would include but are not limited to adult respiratory distress syndrome, reperfusion injury, ischemia, ulcerative coliris, vasculitides, atherosclerosis, inflammatory bowel disease and tumor metastases.

Adhesion receptors are organized into three main families: the selectins, the immunoglobulin superfamily, and the integrins (*Nature*, 346:426 (1990)). Members of all three classes are involved in mediating leukocyte adhesion during inflammation (for reviews of this area see: *Thrombosis and Hemostasis*, 65(3);223 (1991), *Clinical and Experimental Allergy*, 20:619 (1990), *Transplantation*, 48:727 (1989), *Biochemical Pharm*, 40 (8):1683 (1990)). Endothelial leukocyte adhesion molecule-1 (ELAM-1 or E-selectin) is a member of the selectin family of glycoproteins that promote cell-cell adhesion. E-selectin is reported to be maximally expressed on the surface of endothelial cells 4 hours after stimulation of the endothelial cells with cytokines, such as interleukin-1 (IL-1) or tumor necrosis factor α (TNF-α) or other inflammatory mediators, such as lipopolysaccharide (LPS) (*Pro. Nat. Acad. Sci.*, 84:9238 (1987).

Intercellular adhesion molecule-1 (ICAM-1) is a member of the immunoglobulin superfamily. It is also upregulated with maximum expression occurring 12–24 hours after stimulus. It has been shown that 4 hours after the endothelial cells are stimulated with an inflammatory mediator both E-selectin and ICAM-1 are present on the cell surface (*J. Clin. Invest.*, 82: 1746 (1988) and *J. Immun.*, 137:1893 (1986), *Blood*, 78:2721 (1991)).

The benzothiophene, benzofuran and indole thiazepinones, oxazepinones and diazepinones of the present invention have been shown to inhibit the adhesion of neutrophils to human umbilical vein endothelial cells (HUVECS) stimulated with TNFα in an in vitro assay.

SUMMARY OF THE INVENTION

Accordingly, the present invention is a compound of the Formula (I) or a pharmaceutically acceptable acid addition salt thereof:

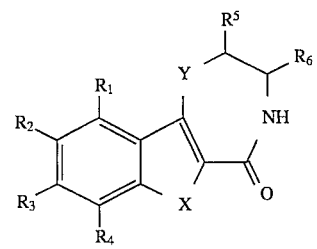

wherein $R_1$, $R_2$, $R_3$, and $R_4$ are each independently hydrogen, hydroxy, halogen, lower alkyl, lower alkoxy, benzyloxy, trifluoromethyl, nitro, or —$NR_8R_9$, in which $R_8$ and $R_9$ are each independently hydrogen or lower alkyl;

$R_5$ and $R_6$ are each independently hydrogen, lower alkyl or phenyl;

X is O, $(O)_n$ or $NR_7$;

Y is O, $S(O)_n$ or $NR_8$;

$R_7$ is hydrogen, lower alkyl, phenyl, benzyl, $CH_2OR_8$ or lower alkyl, phenyl, benzyl substituted with halo;

$R_8$ is hydrogen, lower alkyl or phenyl;

n is an integer of 0, 1 or 2;

with the provisos that 1) when X is NH, Y is NH, $R_1$ is H, $R_3$ is H and $R_4$ is Br, $R_2$ is not methyl;

2) when X is NH, Y is NH, $R_1$, $R_3$ and $R_4$ are H, $R_2$ is not methoxy or ethoxy, and 3) when X is NH, Y is S, at least one of $R_1$, $R_2$, $R_3$ and $R_4$ is not H.

The present invention includes pharmaceutical compositions comprising a therapeutically effective amount of a compound of the Formula I above, together with a pharmaceutically acceptable carrier.

A third aspect of the present invention is a method of treating diseases mediated by inhibiting the adhesion of leukocytes to endothelial cells comprising administering to a host in need thereof a pharmaceutical composition containing a compound of Formula I above in unit dosage form.

A preferred embodiment is a method for treating inflammatory disease in humans comprising administering an antiinflammatory amount of a compound of Formula I.

DETAILED DESCRIPTION

The terms used in defining the compounds of Formula I of the present invention are defined as follows:

Lower alkyl and lower alkoxy mean a straight or branched alkyl or alkoxy group having 1 to 4 carbon atoms and includes, for example, methyl, ethyl, propyl, i-propyl, or otherwise referred to as (methyl)ethyl, and t-butyl or otherwise referred to as 1,1-(dimethyl)ethyl, and correspondingly, for example, methoxy, ethoxy, i-propoxy, or otherwise referred to as 1-(methyl)ethoxy and the like.

Halogen includes fluorine, chlorine, bromine, or iodine.

The compounds of the Formula I are capable of further forming pharmaceutically acceptable acid addition salts. All of these forms are within the scope of the present invention.

Pharmaceutically acceptable acid addition salts of the compounds of Formula I include salts derived from inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, N-methyl glutamine (see, for example, Berge S. M., et al., "Pharmaceutical Salts," *Journal of Pharmaceutical Science*, 66:1–19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

A preferred embodiment of the present invention is a compound of Formula I, wherein $R_1$, $R_3$ and $R_4$ are hydrogen and $R_2$ is as defined above.

A more preferred embodiment of the present invention is a compound of Formula I, wherein $R_1$, $R_3$ and $R_4$ are hydrogen; $R_2$ is hydrogen or lower alkoxy; X is O, $S(O)_n$ or $NR_7$; Y is O or $S(O)_n$; $R_7$ is hydrogen or lower alkyl, and n is 0, 1, or 2.

Particularly valuable are:
2,3-dihydro-9-methoxy-[1]benzothieno[2,3-f]- 1,4-thiazepin-5(4H)-one, 2,3-dihydro-[1]benzothieno[2,3-f]-1,4-oxazepin-5(4H)-one, 2,3-dihydro-9-methoxy-[1]benzothieno[2,3-f]- 1,4-thiazepin-5(4H)-one -1-oxide, 3,4-dihydro-9-methoxy- 6-methyl -2H-1,4-oxazepino[6,7-b]indol-5(6H)-one, 2,3-dihydro-1H-benzothieno-[3,2-e]-1,4-diazepine-5-one, 2,3-dihydro-9-methoxy-1H-benzothieno-[2,3-f] -1,4-oxazepine-5-one, 2,3-dihydro-9-methoxy-6-oxide-1H-benzothieno-[2,3-f]oxazepine-5-one, 2,3-dihydro-9-methoxy-2-methyl-1H-benzothieno-[2,3-f]- 1,4-oxazepine-5-one, 2,3-dihydro-7,8,9,10-tetrachloro- 1H-benzothieno[2,3-f]-1,4-oxazepine-5-one, 3,4-dihydro- 8-nitro-6-tert.-butyl-2H-1,4-oxazepine[6,7-b]indol- 5(6H)-one, 3,4-dihydro -9-isopropoxy-6-phenoxymethyl-2H- 1,4-oxazepine[6,7-b]indol -5(6H)-one hydrochloride, 3,4-dihydro-8,10-dibromo-6-(3-chlorobenzyl-2H- 1,4-oxazepino[6,7-b]indol-5(6H)-one, 2,3-dihydro- 8-chloro-1H-benzofurano[2,3-f]-1,4-oxazepine-5-one, methanesulfonate, 2,3-dihydro-1,2,3-trimethyl-1H-benzofurano[ 3,2-e]-1,4-diazepine-5-one, and 2,3-dihydro-3-hexyl-1H-benzofurano[2,3-f] -1,4-thiazepine-5-one.

For medical use, the amount required of a compound of Formula I or a pharmacologically acceptable acid addition salt thereof to achieve a therapeutic effect will, of course, vary both with the particular compound, the route of administration, the mammal under treatment, and the particular disorder of disease concerned. In a preferred embodiment, the invention provides a method for treating humans suffering from inflammatory disease, such as arthritis or swelling comprising administering an antiinflammatory effective amount to the subject in need of treatment. A suitable dose of a compound of Formula I or a pharmacologically acceptable acid addition salt thereof for a mammal suffering from, or likely to suffer from any condition as described hereinbefore is 0.1 µg to 500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two to three times daily. In the case of topical administration, e.g., to the skin or eye, a suitable dose may be in the range 0.1 ng to 100 µg of the compound per kilogram, typically about 0.1 µg/kg.

In the case of oral dosing for the treatment or prophylaxis of arthritis or inflammation in general, due to any cause, a suitable dose of a compound of Formula I or a physiologically acceptable acid addition salt thereof, may be as specified in the preceding paragraph, but most preferably is from 1 mg to 10 mg of the compound per kilogram, the most preferred dosage being from 1 mg to 5 mg/kg of mammal body weight, for example, from 1 to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of Formula I or a pharmacologically acceptable acid addition salt thereof and a pharmacologically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long-acting formulations known in the art.

The formulations may conveniently be presented in unit dosage form and may be prepared by any of the methods well known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The usefulness of the compounds of the present invention as inhibitors of leukocyte adherence to vascular endothelium and thus in treating inflammatory-related diseases or conditions may be demonstrated by their effectiveness in various standard test procedures. A description of each procedure and exemplary test results follows.

Protocol for the Intercellular Adhesion
Molecule-1/HUVEC Expression Assay (ICAM-1)
and the E-Selectin/HUVEC Expression Assay
(ESEL)

Cell culture

Human umbilical cord endothelial cells (HUVECs) from Clonetics were purchased in T-25 tissue culture flasks and allowed to grow for 1–3 days after arrival at 37° C. and 5% carbon dioxide. The HUVECs were then split by rinsing the T-25 with 10 mL of a 0.025% trypsin/0.01% EDTA for 5–10 seconds, pouring off the rinse solution. Another 10 mL of the trypsin/EDTA solution was added and the cells were agitated for 2–4 minutes while rapping on the side of the flask with a pencil eraser. The contents of the flask were then poured into a 50 mL centrifuge tube containing 40 mL of media. The media was endothelial basal media purchased from Clonetics containing hydrocortisone (2 mg/L), epidermal growth factor (0.05 ug/L), bovine brain extract (12 mg/L) and heat inactivated fetal calf serum (6%) from Hyclone. The cells were centrifuged at 15° C. for 10–15 minutes, the supernatant drained off, and the cells resuspended with fresh media. Cells were washed in an identical manner a second time and then seeded into 96 well tissue culture plates.

Cytokine Stimulation

Within 5 days after reaching confluence the cells were stimulated with tumor necrosis factor alpha (TNFα) (Genzyme) to obtain a final media concentration of 140 U/mL and allowed to incubate at 37° C. for 4 hours. After the 4 hour incubation, the media was removed and stored for analysis of chemokine production. The cells were washed 3 times with calcium and magnesium free phosphate buffered saline. The monocultures were then fixed by adding 10% buffered formalin to the wells for 15 minutes. After fixing, the cells were washed 3 times with Dulbecco's Modified Eagle Media (Gibco) containing 2% bovine serum albumin (DMEM/2%BSA) and refrigerated overnight.

The ELISA

Murine monoclonal anti-human ICAM-1 (R & D Systems, Cat. No. BBA-4) or murine monoclonal anti-human E-selectin (R & D, Cat. No. BBA-2) dissolved in DMEM/2% BSA were added to each well at 0.5 µg/mL and allowed to incubate at 37° C. for 2 hours. HUVEC monocultures were then washed 4 times with DMEM/2%BSA. A peroxidase conjugated sheep anti-mouse IgG (Cappel) was added (1:3,000 dilution) and allowed to incubate 1 hour at 37° C. The cells were then washed 4 times with DMEM. A color reagent (Biorad) was added to the fixed cells and incubated 15 minutes at room temperature. The reaction was stopped with a 2% oxalic acid solution and the absorbance read at 414 nm on a titertek plate reader.

Compound Testing

Compounds were dissolved in DMSA at a concentration of 30 mmol and diluted with media to obtain final testing concentrations. HUVECs received compound dissolved in media 30 minutes before the TNFα challenge. The absorbance of non-stimulated HUVECs was subtracted from the absorbance values of TNFα stimulated cells before percent inhibition was determined. Percent inhibition was determined by comparing the absorbance of vehicle treated cells with drug treated cells. $IC_{50}$s were determined using linear regressoin analysis.

METHOD FOR DETERMINING THE
INHIBITION OF HUMAN NEUTROPHIL
ADHESION TO THE TNF-α STIMULATED
HUMAN UMBILICAL VEIN ENDOTHELIAL
CELLS (ECA)

Cell Culture

Second passage HUVEC (Clonetics Corporation, San Diego, Calif., CC-2617) were seeded into Corning (Corning glass works, Corning, N.Y.) 96-well cell culture plates at approximately $5 \times 10^3$ cells/well and grown to confluency in supplemented endothelial basal medium (EBM MCDB-131, Clonetics, 10 ng/mL EGF, 1 µg/mL hydrocortisone, 0.4% bovine brain extract, 5% Fetal Bovine Serum). One day prior to running the assay, typically 3 days postseeding, the cultures were refed with 0.2 mL/well supplemented EBM (S-EBM).

Preparation of Test Compounds

Test compounds were prepared as 10 mL stock solutions at a concentration of 1.0 mM. The compounds were initially solubilized in 0.1 mL DMSO followed by the addition of 9.9 mL S-EBM. The drug preparations were then diluted in one step to a concentration of 66.6 µM. Solubilizations and dilutions were performed in polystyrene containers.

Stimulation of HUVEC

Recombinant human tumor necrosis factor-α (TNF, Genzyme, Boston, Mass., code TNF-H) was prepared at 400 U/mL in S-EBM. Stock TNF was prepared to 20,000 U/mL in Delbecco's phosphate buffered saline (PBS, Gibco, Grand Island, N.Y.) plus 0.1% BSA and stored at −70° C. HUVEC were washed one time with 0.2 mL warm unsupplemented EBM and then stimulated for 4 hours at 37° C. with 200 U/mL TNF in the presence of 33.3 µM test compound. This was accomplished by adding 0.1 mL of 400 U/mL TNF and 0.1 mL 66.6 µM test compound. These additions were done slowly as to not disrupt the HUVEC monolayer. Each compound was tested in six wells. Unstimulated (vehicle control) and TNF-stimulated without test compound treatments were also run in each plate.

Labeling of Neutrophils

One hour prior to adding the neutrophils to the HUVEC, neutrophils ($5 \times 10^6$/mL) were labeled for 30 minutes at 37° C. with 5 µM calcein-AM (Molecular Probes, Eugene, Oreg.) in Hanks' balanced salt solution plus 0.45% BSA. Stock calcein was prepared to 5 mM in anhydrous DMSO and stored desiccated at −20° C. At the end of the incubation the cells were washed two times in cold HBSS and resuspended to a final concentration of $1 \times 10^6$ cells/mL in supplemented EBM.

Addition of Neutrophils to HUVEC

At the end of the 4-hour stimulation and immediately prior to the addition of the neutrophils to the HUVEC monolayer, the plates were washed with 0.2 mL warm unsupplemented EBM to remove TNF and drug. Neutrophils ($1 \times 10^5$ cells) were slowly added to each of the treated wells and incubated for 30 minutes at 37° C. At the end of the incubation the plates were washed two times with 0.2 mL warm unsupplemented EBM followed by a final addition of 0.1 mL for plate scanning.

Determination of Relative Fluroescence

The relative fluroescence was determined using a Millipore Cytofluor 300 system (excitation=480, emission=530, sensitivity=4).

Calculations

The assay was considered valid if the TNF-stimulation of the HUVEC resulted in a 300% increase in neutrophil adherence over adherence to unstimulated HUVEC. Results were expressed as means of percent inhibitiion of TNF-stimulated adherence.

$$\% \text{ Inhibition} = 100 - \left[ \frac{\text{stimulated adherence}_{(drug)} - \text{unstimulated adherence}}{\text{stimulated adherence}_{(control)} - \text{unstimulated adherence}} \right]$$

Some of these compounds were tested at concentrations of 33.3 μM, 10.0 μM, 3.3 μM, and 1.0 μM to determined $IC_{50}$ values. Linear regression analysis of the means of the inhibition values were used to determine the $IC_{50}$.

The results obtained with certain compounds of the present invention are shown in Table I.

TABLE I 2,3-Dihydro-9-methoxy-[1]benzothieno[2,3-f]-1,4-thiazepin-5(4H)-one

| Example | $R_2$ | X | Y | ECA ($IC_{50}$) | ICAM/ESEL ($IC_{50}$ or % Inhib @ 30 μM) | OM-10 ($IC_{50}$ μM) |
|---|---|---|---|---|---|---|
| 1 | OMe | S | S | 5.2 | 3.1/1.3 | .21 |
| 2 | H | S | O | | 42%/40% | >30 |
| 4 | OMe | NMe | O | | 14.7/14.2 | |
| 5 | H | S | NH | | 64%/47% | |
| 6 | OMe | S | O | | 3.1/7.5 | |
| 7 | OMe | S—O | O | | 30%/30% | |
| 8 | OMe | S | O (2-methyl) | | 3.8/5.3 | |

The invention compounds have also demonstrated activity in standard in vivo assays utilized to measure their ability to inhibit neutrophil influx, and accordingly their utility to treat conditions of inflammation. In one test called the Reverse Passive Arthus Pleurisy Assay, male outbred Wistar rats (220–245 g, Charles River Laboratories) were fasted for 16 to 18 hours. Vehicle (1:1, ethanol:saline) or an invention compound dissolved in vehicle was administered IV. The animals were lightly anesthetized with ether and given an IV injection of 2.5 mg bovine serum albumin (BSA) in saline. Immediately following the IV injection, a small incision was made between the ribs, and 0.2 mL of a rabbit IgG fraction anti-BSA (10 mg/mL in Dulbecco's Phosphate Buffered Saline (PBS)) in PBS was injected into the pleural cavity using a 20-gauge oral dosing needle. The incision was then closed with a 9-mm stainless steel wound clip. Four hours later the animals were euthanized with carbon dioxide and the pleural cavity flushed with 2 mL of a 0.325% phenol red solution in PBS. The exudate-buffer were removed from the pleural cavity for analysis. White blood cells (>90% neutrophils) were counted using a Coulter counter. The pleural exudate volume was measured by a dye dilution method (Carter G. W., et al., *J. Pharm. Pharmacol.* 34:66–67 (1982)). Drug treatment groups were compared to a vehicle-treated group and statistical significance determined using Student's t-test.

When the compound of Example 1 was evaluated in the above test, it exhibited the following inhibitions:

| Dose (mg/kg) | Percent Inhibition of Exudate | Percent Inhibition of Neutrophil Influx |
|---|---|---|
| 0.3 | 40.5 | 18.6 |
| 1.0 | 28.4 | 8.9 |
| 3.0 | 28.2 | 15.9 |

In another in vivo assay called the Thioglycollate-induced neutrophil influx assay, female Balb/c in-bred mice are housed in groups of seven with free access to food and water throughout the study. The animals are orally dosed with vehicle (0.5% hydroxypropyl methyl cellulose with 0.2% Tween 80) or invention compound dissolved or suspended in vehicle. One hour after oral administration, the mice are anesthetized by diethyl ether inhalation and intraperitoneally injected with 1.0 mL of 3% thioglycollate medium in saline. Two hours post-thioglycollate injection, the animals are euthanized by carbon dioxide asphyxiation and injected with 6 mL Dulbecco's PBS containing 10 U/mL sodium heparin and 0.1% BSA. The peritoneal cavity is massaged and an incision is made into the cavity to allow the fluid to be collected into 15-mL centrifuge tubes. An aliquot is removed from each animal and the total number of cells in each aliquot are counted using a Coulter Counter (Model ZBi, Coulter Instruments, Hialeah, Fla.). A second aliquot is removed for microscopy using the Cytospin 2 (Shandon Inc., Pittsburgh, Pa.), and subsequent staining (modified Wright's stain) is performed. Hematologic differentials are performed to determine the percentage of neutrophils which have extravasated to the peritoneal cavity.

When the compound of Example 1 was evaluated in this assay, it exhibited 26.1% inhibition of neutrophil influx at 10 mg/kg, 31.9% inhibition at 30 mg/kg, and 4.3% inhibition at 100 mg/kg.

The compounds of the present invention may be prepared by the following methods.

The first general approach requires as starting materials the 3-hydroxy, thiol, or aminobenzo[b]thiophene, benzofuran or indole -2-carboxylate esters of structure 1 (Scheme 1). The 3-hydroxybenzo[b]thiophene-2-esters are prepared as documented [Connor D. T., et al., *J. Med. Chem.*, 35:958 (1992)]. The 3-thio-benzo[b]thiophene-2-carboxylate esters are prepared by treatment of the analogous 3-chloro derivative [Connor D. T., et al., *J. Med. Chem.*, 35:958 (1992)] with thioacetamide in the presence of a base such as 1,8-diaza-bicyclo[5.4.0]-undec-7-ene (DBU) and a solvent such as N,N'-dimethylformamide or tetrahydrofuran. The 3-amino-benzo[b]thiophene- 2-carboxylate esters are prepared by the known general method [Beck J. R., *J. Org. Chem.*, 37:3224 (1972)]. The 3-hydroxy-indole-2-carboxylate esters are prepared by known methods such as Unangst P. C., et al., *J.. Heterocyclic Chem.*, 24:811 (1987) and Moyer M. P., et al., *J. Org. Chem.*, 51:5106 (1986). The 3-thio-indole- 2-carboxylate esters are prepared by known methods such as Unangst P. C., et al., *J. Heterocyclic Chem.*, 24:811 (1987); Atkinson J. G., et al., *Synthesis*, 480 (1988);

and Nagarajan K., et al. *Indian J. Chem.*, 20B:672 (1981). The 3-amino-indole-2-carboxylate esters are prepared by known methods such as Simakov S.V., et al., *Khim.-Farm. Zu.*, 17:1183 (1983).

The conversion of compounds of type 1 to those of this invention is shown in Scheme 1. The esters are treated with an α-halo-substituted acetonitrile derivative such as bromoacetonitrile in the presence of a base such as potassium t-butoxide in tetrahydrofuran, acetonitrile, or dimethylsulfoxide at 0°–80° C. to provide esters of type 2. The nitrile group is reduced to the corresponding primary amine and the resultant intermediate 3 is cyclized to the lactam 4. The preferred conversion is hydrogenation of 2 with Raney cobalt catalyst in a solvent such as tetrahydrofuran in the presence of a base such as triethylamine at elevated temperature and pressure. Under these conditions 4 is obtained directly from 2. If intermediate 3 is isolated it is cyclized to 4 under basic, preferably NaOMe in methanol, or acidic conditions, preferably polyphosphoric acid, at elevated temperatures.

During the synthesis of some of the invention compounds, it may be necessary or desirable to convert reactive groups such as hydroxy, amino, and carboxy, to derivatives which will protect them from unwanted side reactions when a desired reaction is taking place somewhere else in the molecule. Such protected hydroxy, amino, and carboxy groups are readily deprotected by conventional methods. Commonly used chemical moieties which serve to protect reactive groups such as hydroxy, amino, and carboxy, and methods for their attachment and subsequent removal, are described by Greene and Wuts in *Protective Groups in Organic Synthesis*, John Wiley & Sons, Inc., New York, 1991.

For example, a 3-amino, 3-hydroxy, or 3-thio indole, benzothiophene, or benzofuran (Compound 1 in Scheme 1) can be reacted with a β-halo-ethyleneamine where the amino group is protected with a suitable protecting group (PG) such as a t-butoxycarbonyl (Boc) or benzyloxycarbonyl (Cbz). Reaction under the same conditions as described above provides compounds of type 5. Deprotection (i.e., removal of the PG) of 5 under standard conditions, i.e., trifluoroacetic acid or aqueous acid for the removal of the BOC or hydrogenolysis for removal of the Cbz, provides compounds of type 3 that are cyclized as noted earlier. Another approach is the reaction of compounds of type 1 with ethyleneimine in an alcoholic solvent to directly provide 3 (see: Nagarajan K., et al. *Indian J. Chem.*, 20B:672 (1981)).

A second general approach (Scheme 2) to compounds of type 4 is from the corresponding 3-halo derivatives 6. Reaction of 6 with ethylenediamine and cupric oxide in a solvent such as pyridine in the presence of a base such as potassium carbonate provides compounds of type 3 where Y is NH (see: Hiremath S. P., et al., *Proc. Nat. Acad. Sci., India*, 60:367 (1990)). Reaction of 6 with cysteamine in a solvent such as dimethylformamide in the presence of a base such as DBU provides compounds of type 3 where Y is S. Reaction of 6 with nitroethanol in a solvent such as tetrahydrofuran in the presence of a base such as potassium t-butoxide or potassium hydride provides compounds of type 7. Subsequent reduction of the nitro group to an amine leads to compounds of type 3 where Y is O. In some of the above cases 3 may not be isolated but 4 may be obtained directly.

A third general approach (Scheme 3) also utilizes the 3-halo derivatives 6. The 3-halo derivative is treated with a primary amine that contains a suitably protected amino, hydroxy or thiol group at the β-position, to form an amide group, providing an intermediate of type 7. Deprotection followed by cyclization leads to compounds of type 4. A similar sequence starts with the 3-hydroxy, thiol or amino compound adding an amine with a suitable leaving group at the β-position. The resultant intermediates of type 8 are then cyclized to give 4.

Those compounds of type 4 where X is S and Y is O or NR can be converted to the corresponding sulfoxide and/or sulfone, 9, with an oxidizing agent such as mochloroperbenzoic acid (m-CPBA) or an oxaziridine with the reaction conditions determining the extent of oxidation (Scheme 4). For those compounds of type 4 wherein Y is S, similar oxidation would provide either the sulfoxide or sulfone of type 10.

Conditions within the description of Schemes 1 through 4 and variations in the description are known or can readily be determined from analogous reactions known to one skilled in the art.

SCHEME 1

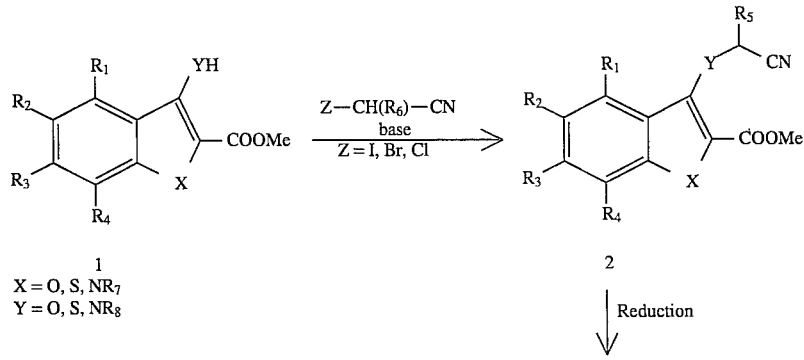

-continued
SCHEME 1
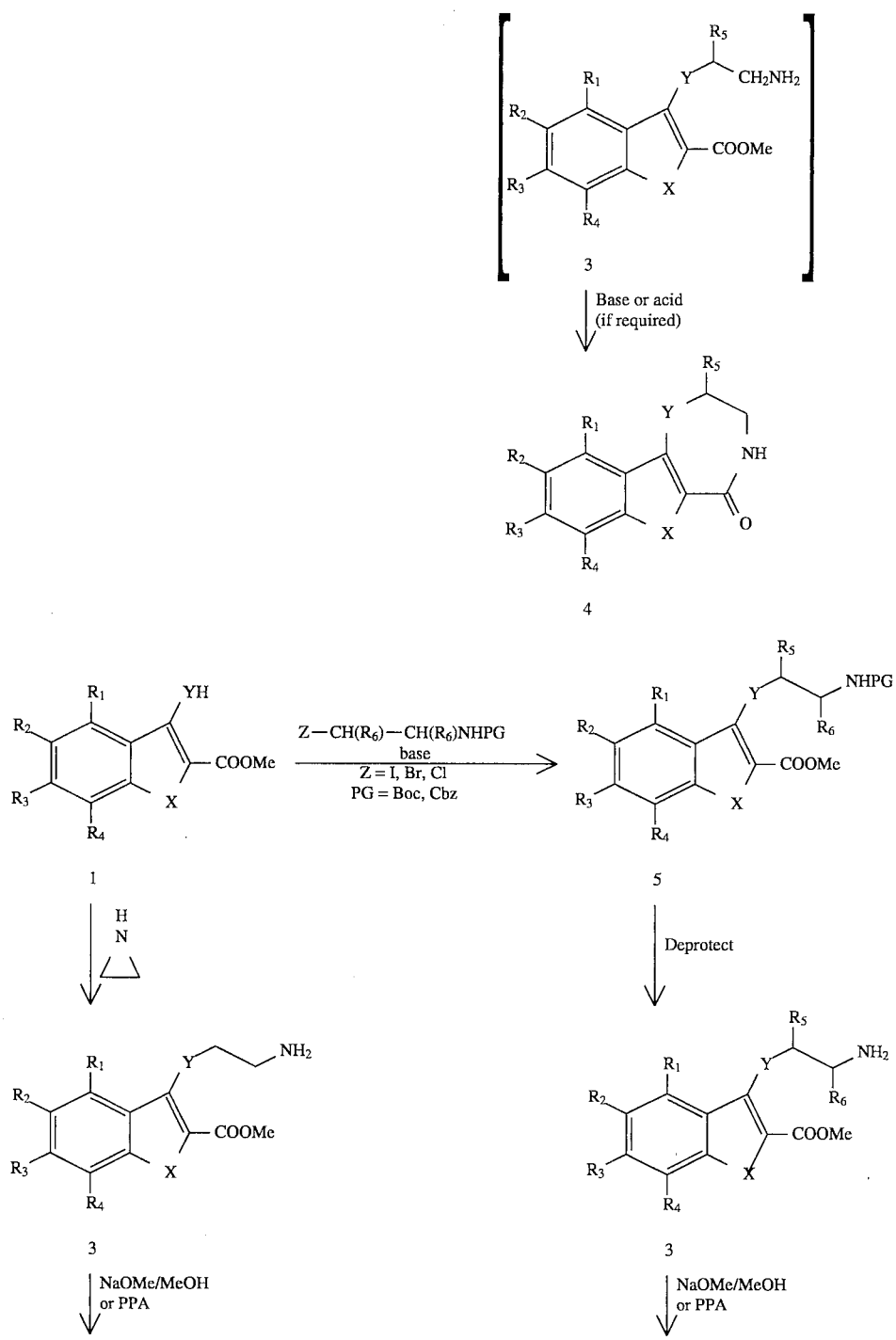

-continued
SCHEME 1
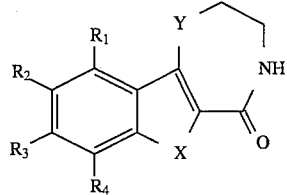
4
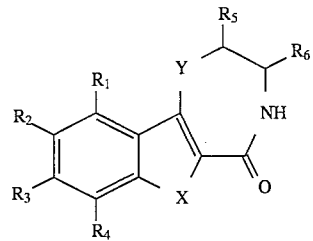
4
SCHEME 2
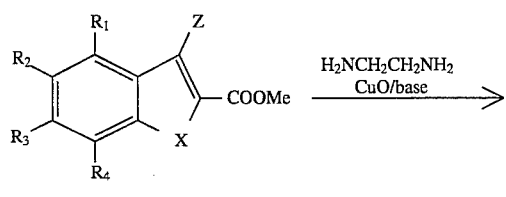 $\xrightarrow{\text{H}_2\text{NCH}_2\text{CH}_2\text{NH}_2}{\text{CuO/base}}$
6
Z = Br, Cl
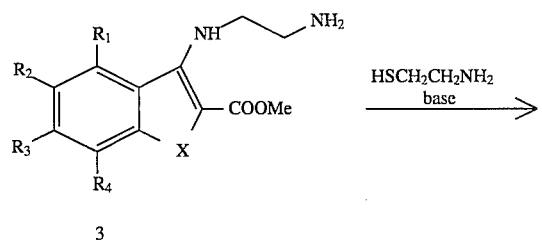 $\xrightarrow{\text{HSCH}_2\text{CH}_2\text{NH}_2}{\text{base}}$
3
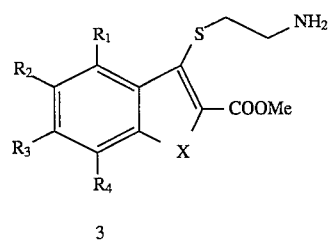 $\xrightarrow{\text{HOCH}_2\text{CH}_2\text{NO}_2}{\text{base}}$
3
-continued
SCHEME 2
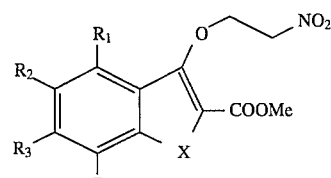
7
↓ reduction
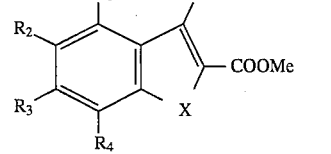
3
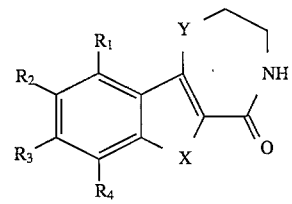 $\xrightarrow{\text{NaOMe/MeOH} \atop \text{or PPA}}$
3
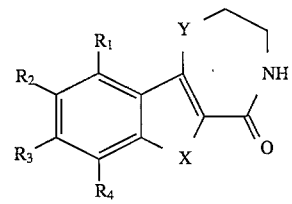
4

SCHEME 3
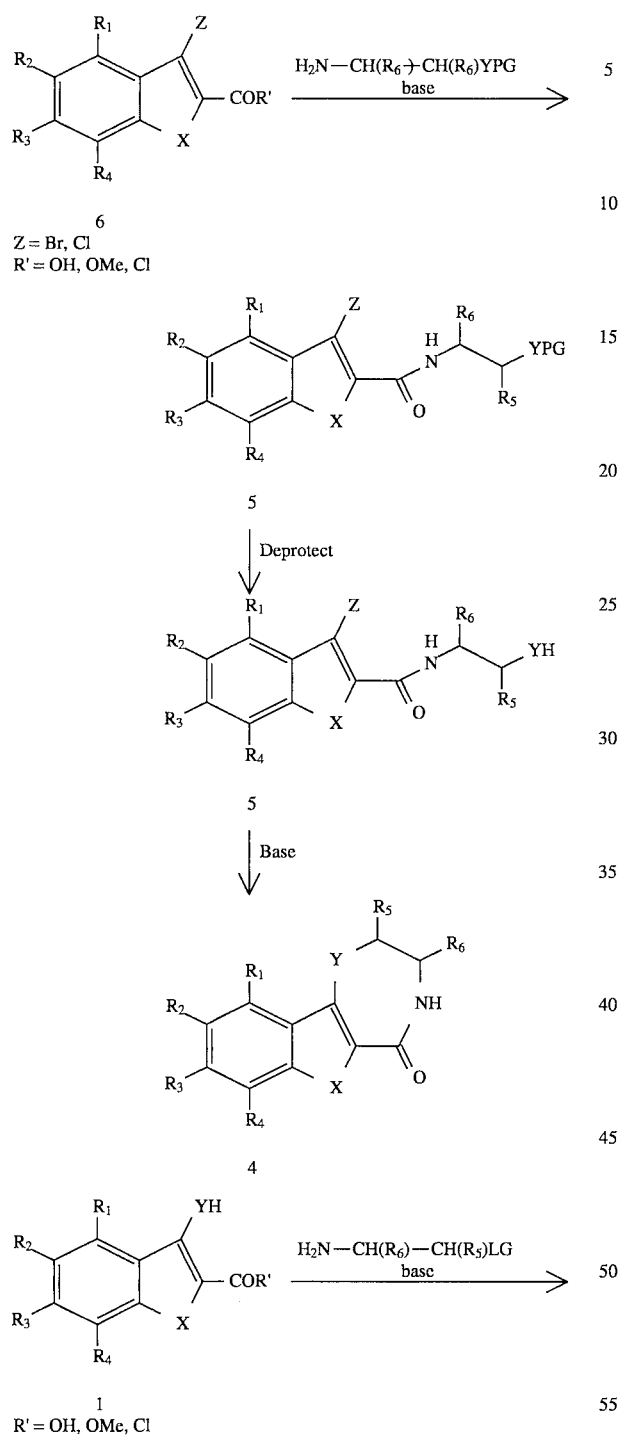
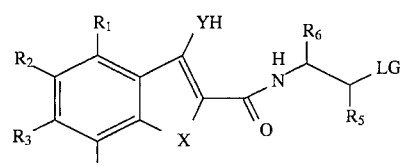
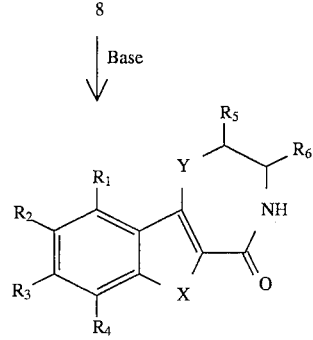
SCHEME 4
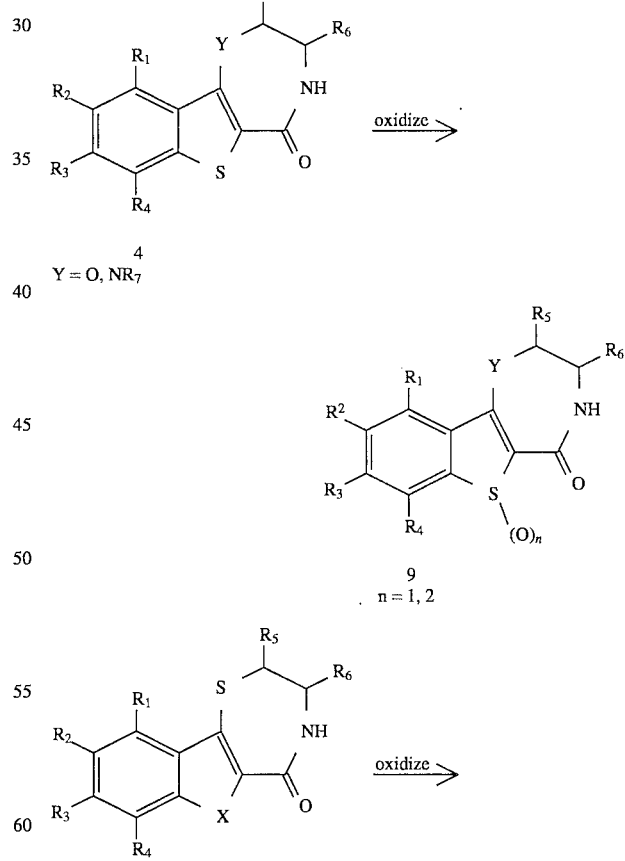

-continued
SCHEME 4

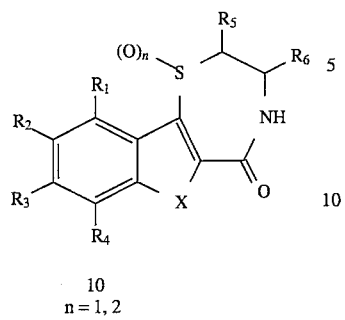

10
n = 1, 2

The following examples are illustrative of the preparation of the compounds of the present invention.

EXAMPLE 1

2,3-Dihydro-9-methoxy[1]benzothieno[2,3-f]-1,4-thiazepin-5(4H)-one

To a room temperature solution of methyl 3-chloro-5-methoxy-benzo[b]thiophene-2-carboxylate (500 mg, 1.95 mmols) [prepared by reaction of the known 3-chloro-5-methoxy-benzo[b]thiophene-2-carbonyl chloride with methanol-[*J. Med, Chem.*, 35:958 (1992)]] in 20 mL of DMF is added cysteamine-HCl (885 mg, 7.79 mmol) followed by DBU (2.33 mL, 15.58 mmol). The reaction mixture is stirred at room temperature for 1.5 hours then warmed to 70° C. The mixture is diluted with ethyl acetate and washed with aqueous HCl, water and brine. The organic layer is dried over MgSO$_4$, filtered and concentrated in vacuo. The crude product is recrystallized from hexane and ethyl acetate to provide 2,3-dihydro-9-methoxy[1]benzothieno[2,3-f]- 1,4-thiazepin-5(4H)-one in 74% yield; mp 209°–209.5° C.

EXAMPLE 2

2,3-Dihydro-[1]benzothieno[2,3-f]-1,4-oxazepin-5(4H)-one

A mixture of the methyl ester of 3-(cyanomethoxy)benzo[b]thiophene-2-carboxylic acid (405 mg, 1.64 mmols) [*J. Hetero. Chem.*, 12:1037 (1975)], 0.5 mL of Et$_3$N and 0.50 g of RaCo in 50 mL of THF is heated at 100° C. under 1200 psi of hydrogen. The reaction mixture is concentrated in vacuo. Column chromatography eluting with a gradient of 1:1 hexane:ethyl acetate to all ethyl acetate provides 2,3-dihydro -[1]benzothieno[2,3-f]1,4-oxazepin-5(4H)-one in 55% yield; mp 244°–245° C.

EXAMPLE 3

2,3-Dihydro-9-methoxy-[1]benzothieno[2,3-f]-1,4-thiazepin-5(4H)-one-1-oxide A mixture of 2,3-dihydro-9-methoxy-[ 1]benzothieno[2, 3-f]-1,4-thiazepin-5(4H)-one (200 mg, 0.75 mmol) and NaBO$_3$-4H$_2$O(116 mg, 0.75 mmol) in 18 mL of AcOH is stirred at room temperature overnight. The reaction mixture is filtered and 60 mL of water is added to the filtrate. Filtration provides 2,3-dihydro-9-methoxy-[1]benzothieno[2,3-f]- 1,4-thiazepin-5(4H)-one-1-oxide in 69% yield; mp 215°–216° C. (dec).

EXAMPLE 4

3,4-Dihydro-9-methoxy-6-methyl-2H-1,4-oxazepino[6,7-b] -indol-5(6H)-one

A. Methyl 3-(cyanomethoxy)-5-methoxy-1-methyl-1H-indole- 2-carboxylate

A suspension of potassium tert-butoxide (3.2 g, 29 mmol) in 60 mL of dimethyl sulfoxide is treated in portions with methyl 3-hydroxy-5-methoxy-1-methyl 1H-indole-2-carboxylate (5.6 g, 24 mmol; Unangst P. C., et al., *J. Heterocyclic Chem.*, 24:811 (1987)) . The mixture is stirred for 15 minutes, and chloroacetonitrile (4.8 mL, 5.7 g, 76 mmol) is added dropwise. The mixture is heated at 80° for 90 minutes, cooled, and added to 800 g of ice and water. The precipitated solid is filtered, washed with 10% methanol-water, and recrystallized from aqueous acetonitrile to give 3.9 g (60%) of product; mp 136°–137° C.

B. A mixture of methyl 3-(cyanomethoxy)-5-methoxy-1-methyl-1H-indole-2-carboxylate (0.60 g, 2.2 mmol) and triethylamine (0.40 mL, 0.29 g, 2.9 mmol) in 35 mL of tetrahydrofuran in a pressure reaction vessel is treated with Raney cobalt catalyst (0.40 g). The reactor is pressurized with hydrogen (590 psi) and heated at 80° C. for 10 hours. The cooled reaction mixture is filtered and the filtrate evaporated. The oil residue is dissolved in 50 mL of methanol, and sodium methoxide (0.80 g, 15 mmol) is added to the solution. The mixture is heated at reflux for 3 hours, then cooled and evaporated. The residue is distributed between 75 mL of ethyl acetate and 150 mL of brine. The aqueous layer is extracted several times with fresh ethyl acetate. The combined organic layers are washed with brine, dried (anhydrous sodium sulfate) and evaporated. The crude product residue is purified by flash chromatography (silica gel, 5% methanol in dichloromethane elution) to yield 0.18 g (33%) of product. A sample recrystallized from ethyl acetate-hexane has mp 184°–186° C.

EXAMPLE 5

2,3-Dihydro-1H-benzothieno-[3,2-e]-1,4-diazepine-5-one 3-(2-Aminoethylamino)benzo[b]thiophene-2-carboxylic acid methyl ester hydrochloride A solution of 2-(4,5-dihydro-1H-imidazol- 2-yl)benzenethiol (1.00 g, 5.62 mmol) [Hegen, H., Fleig, H. *Justus Liebigs Ann. Chem.* 11:1994 (1975)] and chloromethyl acetate (610 mg, 5.62 mmol) in 15 mL of methanol is heated at reflux for 90 minutes. The reaction is cooled to room temperature and filtered. The filtrate is concentrated to dryness and the residue dissolved in hot chloroform. After several hours the resulting precipitate is collected and dried. The mother liquor affords a second crop of crystals giving 3-(2-aminoethylamino)benzo[b]thiophene-2-carboxylic acid methyl ester hydrochloride in an overall yield of 61%, mp 219°–220° C.

2,3-Dihydro-1H-benzothieno-[3,2-e]-1,4-diazepin-5-one

A solution of 3-(2-aminoethylamino)benzo[b] -thiophene-2-carboxylic acid methyl ester hydrochloride (339 mg, 1.18 mmol) and freshly prepared sodium methoxide (from 134 mg, 2.48 mmol of sodium) in 5 mL of methanol is heated at reflux for 18 hours. Upon cooling, the reaction is neutralized with 25 mL of 1N HCl and cooled to 0° C. for 1 hour. The resulting yellow crystalline material is filtered and dried under vacuum at 60° C. for several hours to provide 2,3-dihydro-1 H-benzothieno-[3,2-e]-1,4-diazepin-5-one in 64% yield. Chromatography, eluting with a gradient of 2% methanol in ethyl acetate in 5% methanol in ethyl acetate, gives analytically pure, 2,3-dihydro-1H-benzothieno-[3,2-e]- 1,4-diazepin-5-one, mp 210°–212° C.

EXAMPLE 6

2,3-Dihydro-9-methoxy-1H-benzothieno-[2,3-f]-1,4-oxazepin-5-one

3-Cyanomethoxy-5-methoxy-benzo[b]thiophene-2-carboxylic acid methyl ester

To a room temperature solution of methyl 3-hydroxy-5-methoxybenzo[b]thiophene-2-carboxylate (1.00 g, 4.2 mmol) [Connor, et al., *J. Med. Chem.* 35:959 (1992)]in 20 mL of DMSO is added potassium t-butoxide (494 mg, 4.41 mmol) followed by bromoacetonitrile (878 μL, 12.58 mmol). The mixture is stirred at room temperature for 1.5 hours, then poured into ethyl acetate and 1N HCl. The organic layer is washed with 1N HCl, followed by several portions of brine, and dried over $MgSO_4$. Filtration followed by removal of solvent in vacuo and recrystallization of the residue from ethyl acetate:hexane gives 413 mg. additional crop of 112 mg can be obtained from the mother liquor, mp 159.5°–160° C.

2,3-Dihydro-9-methoxy-1H-benzothieno-[2,3-f]- 1,4-oxazepin-5-one

A solution of 3-cyanomethoxy-5-methoxy-benzo[b]-thiophene-2-carboxylic acid methyl ester (2.5 g, 9.0 mmol) in 50 mL of THF is heated to vigorous reflux. Borane-dimethyl sulfide (9.0 mL, 90.2 mmol) is rapidly added and heating continued for 25 minutes with THF being added as it evaporates. An additional amount of borane-dimethyl sulfide (4.0 mL) is added and heating continued for 10 minutes. The reaction mixture is cooled to 0° C. and 50 mL of 6N HCl is carefully added. Hydrogen gas is evolved and the temperature of the reaction mixture increases. The resultant precipitate is collected by filtration, washed with water, and dried in vacuo overnight.

The solid (2.3 g, 8.2 mmol) is added to a freshly prepared solution of sodium methoxide (from 1.9 g, 82.0 mmol of sodium) in 40 mL of methanol. The reaction mixture is warmed to 50° C. for 2 hours, then heated at reflux for 2 hours. After cooling to room temperature, the precipitate is collected and washed with cold methanol, followed by cold diethyl ether. The solid is dried in vacuo overnight to give 1.18 g (52%). An analytical sample of 2,3-dihydro-9-methoxy- 1H-benzothieno-[2,3-f]-1,4-oxazepin-5-one is obtained by recrystallization from ethyl acetate:hexane, mp 264°–265° C.

EXAMPLE 7

2,3-Dihydro-9-methoxy-6-oxide-1H-benzothieno-[2,3-f]-1,4-oxazepin-5-one

To a suspension of 2,3-dihydro-9-methoxy-1 H-benzothieno-[2,3-f]-1,4-oxazepin-5-one (1.00 g, 4.0 mmol) in 100 mL of warm methanol is added 30% hydrogen peroxide (8.0 mL, 80 mmol) followed by selenium dioxide (445 mg, 4.01 mmol). The reaction mixture is stirred at room temperature for 3 hours then heated at 30° C. for 1.5 hours followed by heating at 40° C. for 2 hours. The reaction mixture is cooled to −40° C. and the resulting precipitate is collected by filtration. The residue is chromatographed eluting initially with 5% methanol in ethyl acetate gradually increasing the solvent polarity to 1:1 methanol:ethyl acetate to give 338 mg of product. An analytical sample of 2,3-dihydro-9-methoxy-6-oxide-1H-benzothieno-[ 2,3-f]-1,4-oxazepin-5-one is obtained by recrystallization from methol:ethyl acetate, mp 273°–274° C.

EXAMPLE 8

2,3-Dihydro-9-methoxy-2-methyl-1H-benzothieno-[2,3-f]- 1,4-oxazepin-5-one 3-(1-Cyanoethoxy)-5-methoxy-benzo[b]thiophene-2-carboxylic acid methyl ester To a room temperature solution of methyl 3-hydroxy-5-methoxybenzo[b]thiophene-2-carboxylate (1.00 g, 4.2 mmol) [Connor, et al., *J. Med. Chem.* 35:958 (1992)] in 20 mL of DMSO is added potassium t-butoxide (494 mg, 4.41 mmol) followed by 2-chloropropionitrile (1.1 mL, 12.6 mmol). The mixture is stirred at room temperature for 1.5 hours then warmed to 82° C. for 3 hours. The reaction mixture is poured into ethyl acetate and 1N HCl. The organic layer is washed with 1N HCl, followed by several portions of brine and dried over $MgSO_4$. Filtration followed by removal of solvent in vacuo and recrystallization of the residue from ethyl acetate:hexane gives 853 mg, mp 127°–129° C.

2,3-Dihydro-9-methoxy-2-methyl-1H-benzothieno-[ 2,3-f]-1,4-oxazepin-5-one

A solution of 3-(1-cyanoethoxy)-5-methoxybenzo[b]-thiophene-2-carboxylic acid methyl ester (400 mg, 1.37 mmol) in 10 mL of THF is heated to vigorous reflux. Borane-dimethyl sulfide (1.4 mL, 13.7 mmol) is added dropwise and heating continued for 20 minutes with THF being added as it evaporates. The reaction mixture is cooled to room temperature and 7.5 mL of 6N HCl is carefully added. After 5 minutes the reaction mixture is cooled to 0° C. and 68.5 mL of 1N NaOH is added followed by ethyl acetate. The layers are separated and the organic phase is washed with 1:1 brine:water, then with additional brine. The organic phase is dried over $MgSO_4$, filtered, and concentrated in vacuo. The residue is chromatographed eluting with a gradient of 5:25:70 methanol:hexane:chloroform to 10:90 methanol:chloroform to 30:70 methanol:chloroform to give 135 mg of product. An analytical sample of 2,3-dihydro-9-methoxy-2-methyl-1H-benzothieno-[2,3-f]- 1,4-oxazepin-5-one is obtained by recrystallization from ethyl acetate:hexane, mp 185°–186° C.

The invention compounds are readily formulated with common diluents and carriers for convenient oral or parenteral administration to humans and animals for treatment of diseases such as inflammation, especially arthritis and the like. The following examples illustrate the preparation of typical pharmaceutical formulations.

EXAMPLE 9

Preparation of 250-mg Capsule 2,3-Dihydro-9-isopropoxy-7-chloro-1H-benzothieno-[2,3-f]-1,4-oxazepin-5-one (250 mg), is blended to uniformity with 150 mg of lactose and 150 mg of corn starch. The mixture is encapsulated into gelatin capsules. Such capsules are orally administered at the rate of one to three each day for treatment of arthritis.

EXAMPLE 10
Formulation for Oral Suspension

| Ingredient | Amount |
| --- | --- |
| 2,3-Dihydro-8-ethyl-10-trifluoro-methyl-6-oxide-1H-benzothieno-[2,3-f]-1,4-oxazepin-5-one | 500 mg |
| Sorbitol solution (70% N.F.) | 40 mL |
| Sodium benzoate | 150 mg |
| Saccharin | 10 mg |
| Cherry Flavor | 50 mg |
| Distilled Water q.s. ad. | 100 mL |

The sorbitol solution is added to 40 mL of distilled water and the oxazepinone is suspended thereon. The saccharin, sodium benzoate, and flavoring are added and dissolved. The volume is adjusted to 100 mL with distilled water. Each milliliter of syrup contains 5 mg of the oxazepinone. This oral formulation is ideally suited for treating inflammation in pediatric care.

EXAMPLE 11

Preparation of Parenteral Solutions

In a solution of 700 mL of propylene glycol and 200 mL of distilled water for injection is dissolved 20.0 g of 2,3-dihydro-7-dimethylamino-1H-benzothieno-[3,2-e]-1,4-diazepin-5-one. The pH of the solution is adjusted to 5.5 with hydrochloric acid, and the volume is made up to 1000 mL with distilled water. The formulation is sterilized, filled into 5.0 mL ampoules each containing 2.0 mL (representing 40 mg of active diazepinone) and sealed under nitrogen. The formulation is administered intravenously to patients suffering from inflammation or AIDS.

EXAMPLE 12

Preparation of Topical Cream

Five hundred milligrams of 2,3-dihydro-7-ethoxybenzofurano-[2,3-f]-1,4-oxazepin-5-one is mixed with 15 g of cetyl alcohol, 1 g of sodium lauryl sulfate, 40 g of liquid silicone D.C. 200 (sold by Dow Corning Co., Midland, Mich.), 43 g of sterile water, 0.25 g of methylparaben, and 0.15 g of propylparaben. The mixture is warmed to about 75° C. with constant stirring, and then cooled to room temperature at which it congeals. The preparation is applied to the skin surface of a person suffering from inflammation.

We claim:

1. A method for treating inflammatory disease in humans comprising administering an antiinflammatory amount of a compound of the formula

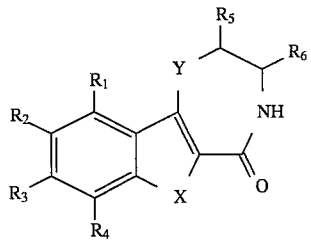

or a pharmaceutically acceptable acid addition salt thereof, wherein $R_1$, $R_2$, $R_3$, and $R_4$ are each independently hydrogen, hydroxy, halogen, lower alkyl, lower alkoxy, benzyloxy, trifluoromethyl, nitro, or —$NR_8R_9$, in which $R_8$ and $R_9$ are each independently hydrogen or lower alkyl;

$R_5$ and $R_6$ are each independently hydrogen, lower alkyl or phenyl;

X is O, $S(O)_n$ or $NR_7$;

Y is O, $S(O)_n$ or $NR_8$;

$R_7$ is hydrogen, lower alkyl, phenyl, benzyl, $CH_2R_9$ or lower alkyl, phenyl, benzyl substituted with halo;

$R_8$ is hydrogen, lower alkyl or phenyl;

n is an integer of 0, 1 or 2;

with the provisos that 1) when X is NH, Y is NH, $R_1$ is H, $R_3$ is H and $R_4$ is Br, $R_2$ is not methyl;

2) when X is NH, Y is NH, $R_1$, $R_3$ and $R_4$ are H, $R_1$ is not methoxy or ethoxy, and 3) when X is NH, Y is S, at least one of $R_1$, $R_2$, $R_3$ and $R_4$ is not H.

2. A method according to claim 1 employing a compound wherein $R_1$, $R_3$ and $R_4$ are hydrogen.

3. A method according to claim 2 employing a compound wherein $R_2$ is hydrogen or lower alkoxy; X is O, $S(O)_n$ or $NR_7$; Y is O or $S(O)_n$;

$R_7$ is hydrogen or lower alkyl, and n is 0, 1 or 2.

4. A method according to claim 3 employing a compound selected from 2,3-dihydro-9-methoxy-[1]benzothieno[2,3-f]-1,4-thiazepin-5(4H)-one;

2,3-dihydro-[1]benzothieno-[2,3-f]-1,4-oxazepin-5(4H)-one;

2,3-dihydro-9-methoxy-[1]benzothieno[2,3-f]-1,4-thiazepin-5(4H)-one- 1-oxide;

3,4-dihydro-9-methoxy-6-methyl-2H-1,4-oxazepino[6,7-b]-indol- 5(6H)-one;

2,3-dihydro-1H-benzothieno-[3,2-e]-1,4-diazepine-5-one;

2,3-dihydro-9-methoxy-1H-benzothieno-[2,3-f]-1,4-oxazepin-5-one;

2,3-dihydro-9-methoxy-6-oxide-1H-benzothieno-[2,3-f]-1,4-oxazepin-5-one; or 2,3-dihydro-9-methoxy-2-methyl-1H-benzothieno-[2,3-f]-1,4-oxazepin-5-one.

* * * * *